United States Patent
Dittgen et al.

[11] Patent Number: 6,117,450
[45] Date of Patent: Sep. 12, 2000

[54] METHOD OF MAKING A PERORALLY ADMINISTERED SOLID DRUG WITH CONTROLLED EFFECTIVE INGREDIENT DELIVERY

[75] Inventors: Michael Dittgen, Apolda; Sabine Fricke, Jena; Carsten Timpe, Weissenborn; Hagen Gerecke; Annette Eichardt, both of Jena, all of Germany

[73] Assignee: JENAPHARM GmbH & Co. KG, Jena, Germany

[21] Appl. No.: 09/065,863

[22] Filed: Apr. 24, 1998

[30] Foreign Application Priority Data

Apr. 29, 1997 [DE] Germany ............. 197 18 012

[51] Int. Cl.$^7$ ............... A61K 9/22; A61K 9/26; A61K 9/28; A61K 9/48; A61K 9/52
[52] U.S. Cl. ............. 424/451; 424/457; 424/458; 424/459; 424/468; 424/469; 424/470; 424/474; 424/475
[58] Field of Search ............ 424/451, 468, 424/469, 474, 457, 458, 459, 470, 475

[56] References Cited

U.S. PATENT DOCUMENTS 5,229,131 7/1993 Amidon et al. ............. 424/451

FOREIGN PATENT DOCUMENTS 44 43 175 A1  6/1996  Germany.
0 719 555 A2  7/1996  Germany.

OTHER PUBLICATIONS

Mutschler, E., et al: "Arzneimittelwirkungen", Lehrbuch der Pharmakologie and Toxikologie, 7. Aufl. Wissemschdftliche Verlagsgesekkschaft mbH Stuttgart 1996, s. 12.
Bauer, K. H., et al: Pharmazeutische Technologie, 4. Auflage, Georg Thieme Verlag Stuttgart, New York, 1993, s. 357–358.
Nuernberg, E. und Surmann, P.: hagers handbuch, bD. 2–Metoden, 5. vollst.neubearb. Auf., Springer Verlag Berlin, Heidelberg, New York, 1991, s. 1122–1123.
Ouriemchi, E. M., et al: "Oral dosages Forms with a Core and Shell with the Same Polymer Containing Different Drug Concentrations", Int. J. Pharm 102, s. 47–54 4–93.
Diluccio, R.C., et al: "Susteined–Release Oral Delivery of Theophylline by Use of Polyvinyl Alcohol and Polyvinyl . . . ", J. Phar. Scien., 83 (1994), pp. 104–106.
Meshali, M., M., et al: "Preparation and Evalution of Theophylline Sustained–Release Tablets", Drug Develop. Ind. Pharm, 22 (1996), pp. 373–376.
Junginger, H. E.: "Oral Applications of Pulsatile Drug Delivery", Pulsatile Drug Delivery, Ed. 1. Wissenschaftliche Verlagsgesellschaft mbH, Stuttgart, 1993, pp. 113–134.
Bauer, K. H., et al: "Coted Pharmaceutical Dosage Forms", CRC Press, New York, Washington, D.C., medpharm Scientific Publishers, Stuttgart, 1998, pp. 222–225, 230,231.
U.S.P. 23<724>, 1996–1997, USPC, Inc.

Primary Examiner—James M. Spear
Attorney, Agent, or Firm—Michael J. Striker

[57] ABSTRACT

The method of making a solid drug with controlled effective ingredient delivery for oral administration includes selecting a predetermined number of at least three of four compressed compositions containing an effective ingredient or effective ingredient combination defined by their release profile of effective ingredient and/or effective ingredient combination. The solid drug or medicinal preparation is formed according to known methods requiring only comparatively small apparatus expense and minimal time. Perorally administered solid drugs are made by this process which can provide widely varying pharmaceutically-required release profiles of effective ingredients or effective ingredient combinations, for example delayed release, uniformly maintained release or pulsatile release adjusted to fit a special rhythm.

8 Claims, 4 Drawing Sheets

METHOD OF MAKING A PERORALLY ADMINISTERED SOLID DRUG WITH CONTROLLED EFFECTIVE INGREDIENT DELIVERY

BACKGROUND OF THE INVENTION

The present invention concerns a method of making a solid drug with controlled effective ingredient delivery for oral administration, in which at least three compressed compositions containing an effective ingredient or effective ingredient combination, variable in their number, are selected from four compressed compositions and are processed to form the drug according to known methods with reduced apparatus work and for a comparatively short time.

Perorally administered medicinal preparations or drugs that have the most widely varied pharmaceutically-required release profiles for their effective ingredients or active ingredient combinations, for example a time-delayed release, a uniformly maintained release or a pulsatile release at a special rhythm, are prepared using the method according to the invention.

The release profile is the variation or dependence of the release (delivery) of the effective or active ingredient or effective ingredient combination on time.

It is the aim of pharmaceutical technology to find methods for converting a pharmaceutically effective ingredient into a drug or medicinal preparation, which guarantees, among other things, a therapeutic release or delivery of the effective ingredient according to the application. An optimum concentration behavior for the particular therapy involved at the active site should therefore be obtained. Ideal mechanisms, in which the active ingredient release is directly controlled by the actual effective ingredient concentration at the active site or by a biochemically variable characteristic of a disease condition, are only useable in the most rare cases.

Known processes and techniques for making solid perorally administered drugs with controlled effective ingredient delivery provide a time-delayed release of an active ingredient, a uniformly maintained release of the effective ingredient or a pulsatile release of the effective material at a special predetermined rhythm.

A uniformly maintained release following a rapid release of an initial dosage of the effective ingredient would however also be conceivable. A maker of this type of drug must thus use several of these types of methods and techniques keep the equipment for them on hand and several special auxiliary substances, which are used for the individual methods, must be ordered and analyzed.

Methods and techniques for making solid perorally administered drugs with a controlled effective ingredient release are known from the professional and patent literature, which should provide many of the above-named release profiles on the basis of a control principle.

It is problematic that perorally administered solid drugs ('single unit' form) with a dwell time of longer than 1 h in the stomach-intestinal tract cannot pass certain positions because of the prevailing variables or conditions according to E. Mutschler, et al, in 'Drug Action' (Arneimittelwirkung), Textbook of Pharmacology and Toxicology, 7th Ed., Scientific Press GmbH, Stuttgart, 1966, p. 12. There is a danger that a large gastric-juice-resistant-coated tablet cannot leave the stomach.

According to K. H. Bauer, Pharmaceutical Technology, 4th Edition, George Thieme Press(Georg Thieme Verlag), Stuttgart, N.Y., 1993, p. 257 retarded 'single-unit' forms however have the advantage of a homogeneous matrix.

Drugs in 'multiple-unit' form decompose chiefly in the stomach in sub-units, granulates or pellets.

A disadvantage in the manufacture of the 'multiple-unit' form is the following: Pellets and granulates are filled in metered volumes in a capsule. The error in filling thus amounts to at least one pellet or grain. Mini-tablets are also used as fill in capsules. Mini-tablets required special presses and put a very high demand on the formulation.

Also E. Nürnberg and P. Surmann (Hrsg.) point out the clear differences between the monolithic 'single-unit' forms and the 'multiple-unit' forms of the respective drugs regarding the passage time through the stomach in HAGERS HANDBOOK, Vol. 2, METHODS, 5th complete reprinting, Springer Press (Springer Verlag), Heidleberg, N.Y., 1991, p. 1123.

The variables controlling the delivery of the effective ingredient in most cases are the osmotic process, the diffusion processes and/or erosion processes. Several of the above-mentioned principles act simultaneously in medicinal preparations with controlled effective ingredient release, for example with a monolithic matrix, swellable hydrogel matrix or coating, according to E. M. Ouriemchi, et al, in 'Oral Dosage Forms with a Core and Shell with the Same Polymer Containing Different Drug Concentrations', Int. J. Pharm. 102 (1994), pp. 47 to 54.

R. C. Diluccio, et al, 'Sustained-Release Oral Delivery of Theophylline by Use of Polyvinyl Alcohol and Polyvinyl Alcohol-Methyl Acrylate Polymers', J. Pharm. Scien., 83 (1994), p. 104–106, describes the controlled delayed release of the effective ingredient, theophylline, by use of a mixture of polyvinyl alcohol (PVA) and a polyvinyl alcohol methacrylate (PVA-MA) copolymer with lower crystallinity. While PVA alone would provide a release which is too rapid, it was found that PVA-MA made a delayed release of effective ingredient possible. It was found that a mixture in the ratio PVA:PVA-MA was 1:9:10 provided the desired delayed delivery of effective ingredient so that the tablets achieved a bioavailability of close to 80% in a test in dogs.

The delayed release of theophylline based on a combination of different polyacrylates which form a mixed barrier around the drug and lead to a matrix diffusion-controlled release of the active ingredient is described in M. M. Mesalie, et al, 'Preparation and Evaluation of Theophylline Sustained-release Tablets', Drug Develop. Ind. Pharm., 22 (1966), pp. 373–376. This drug contains 50% theophylline, Carbopol® 974P as retarding additive, spray-dried lactose and 0.5% lubricant. Only two of the usual release profiles are possible with this principle, a zero order release of effective ingredient that behaves largely linearly, i.e. equal effective ingredient amounts are delivery in equal time intervals, and a release which is proportional to the square root of the time.

H. E. Junginer, 'Oral Applications of Pulsatile Drug Delivery' in R. Gurny, H. E. Juninger, M. A. Peppas (Hrsg.), Pulsatile Drug Delivery, 1st Edition, Scientific Press GmbH (Wissenschaftliche Verlagsgellschaft mbH), Stuttgart, 1993, pp. 113–134 describes several systems for obtaining pulsatile release profiles for the active ingredient, such as coated tablets, pellets or microspheres, OROS®, PULSINCAP®; time-controlled explosion systems, and special layered tablets. Manufacture of these drugs basically involves a great deal of effort and the satisfactory functioning of the system depends chiefly on the exact maintenance of certain production parameters, such as the coating layer thickness, the precision of the release openings and/or the coating, the hydrogel properties, the exact dimensions and if necessary the age of the gels, the exact formulation of the osmotic core material and the outer coating and the precision of the pressing and accuracy of the resulting layer thickness. This process thus has all the considerable disadvantages that special manufacturing methods have. Expensive apparatus and cost intensive precision manufacturing are required.

A pulsatile drug whose effective ingredient release is adjusted to the illness or pain occurring is described in German Patent Document DE 44 43 175 A1. European Patent Document EP 0 719 555 A2 describes the use of melatonin for making peroral pulsatile drugs. This pulsatile drug is in the form of a capsule. It contains the effective ingredient imbedded in different carrier materials. However no compressate or compressed composition was specially formulated which releases the active ingredient in specific amounts. Furthermore this pulsatile drug is not claimed for use with an effective ingredient combination. From the examples provided in DE 44 43 175 A2 it appears that the active ingredient melatonin was imbedded in collagen spheroids. These collagen spheroids were dispersed with an additional amount of melatonin in peanut oil. The filling of this type of multi-dispersion oily system in capsules requires special techniques, know-how and apparatus, which are usually not available to most pharmaceutical manufacturers.

SUMMARY OF THE INVENTION

It is an object of the present invention to provide a method of making a perorally administered solid drug with controlled effective ingredient release, with which any pharmaceutically-required release profile can be obtained and the drug is made with reduced apparatus expense and in a comparatively shorter time.

According to the invention, four different types of compressed compositions having respective different amounts and/or types of effective ingredients and/or effective ingredient combinations are made available, a predetermined number, advantageously up to 30, of the compressed compositions are selected from at least three different types of the compressed compositions out of the four available, the selected compressed compositions are mixed with pharmaceutically compatible auxiliary and/or carrier substances, granulated, formed into tablets and coated, so that a predetermined pharmaceutically-required release profile of the effective ingredient and/or effective ingredient combination is produced.

A first compressed composition A of the four different available compressed compositions is formed to provide a rapid release of the effective ingredient and/or effective ingredient combination in which at least 75% of its effective ingredient content is delivered within 45 minutes.

A second compressed composition B is formed to provide an effective ingredient and/or effective ingredient combination release according to a uniformly maintained release profile in which 100% of its effective ingredient is delivered at the earliest within 3 hours according to a release profile which is approximately zero order. The effective ingredient and/or effective ingredient combination release should be largely linear which means that equal amounts of effective ingredient are delivered in equal time intervals. This type of release profile of the effective ingredient and/or the effective ingredient combination could be obtained by, among other things, hydrophilic matrix tablets, diffusion controlling lacquer coatings or lipophilic matrix tablets.

A third compressed composition C provides a time-delayed release. This compressed composition delivers at least 75% of its effective ingredient and/or effective ingredient combination within 45 minutes in the duodenum and intestine at a pH of 6 to 7.5. Usually this type of release profile of the effective ingredient or ingredients can be achieved by coating a fast release tablet similarly to the compressed composition A with a gastric-juice-resistant coating, for example based on a polymethylmethacrylate or shellac.

A fourth compressed composition D has a release profile of effective ingredient and/or a combination of effective ingredients, which combines delaying aspects with uniformly maintained release aspects. One hundred percent of the effective ingredient is delivered at the earliest 3 hours after reaching a pH of from 6 to 7.5 according to a release profile of approximately zero order suitable for the situation in the duodenum and intestine. Release profiles, which can combine delayed release aspects with uniformly maintained release aspects, among other things, are obtained with gastric-juice-resistant coated hydrophilic matrix tablets or by combinations of gastric-juice resistance with diffusion controlled lacquer coatings.

Advantageous embodiments of this invention include a capsule for oral administration of the drug. This capsule has the advantage of being a 'multiple-unit' form.

The compressed compositions preferably have a weight of from 30 to 600 mg, especially from 40 to 100 mg. The solid drug advantageously has a weight of up to 1 g.

BRIEF DESCRIPTION OF THE DRAWINGS

The objects, features and advantages of the invention will now be illustrated in more detail with the aid of the following description of the preferred embodiments, with reference to the accompanying figures in which.

DETAILED DESCRIPTION OF THE PREFERRED EMBODIMENTS

Figure 1:
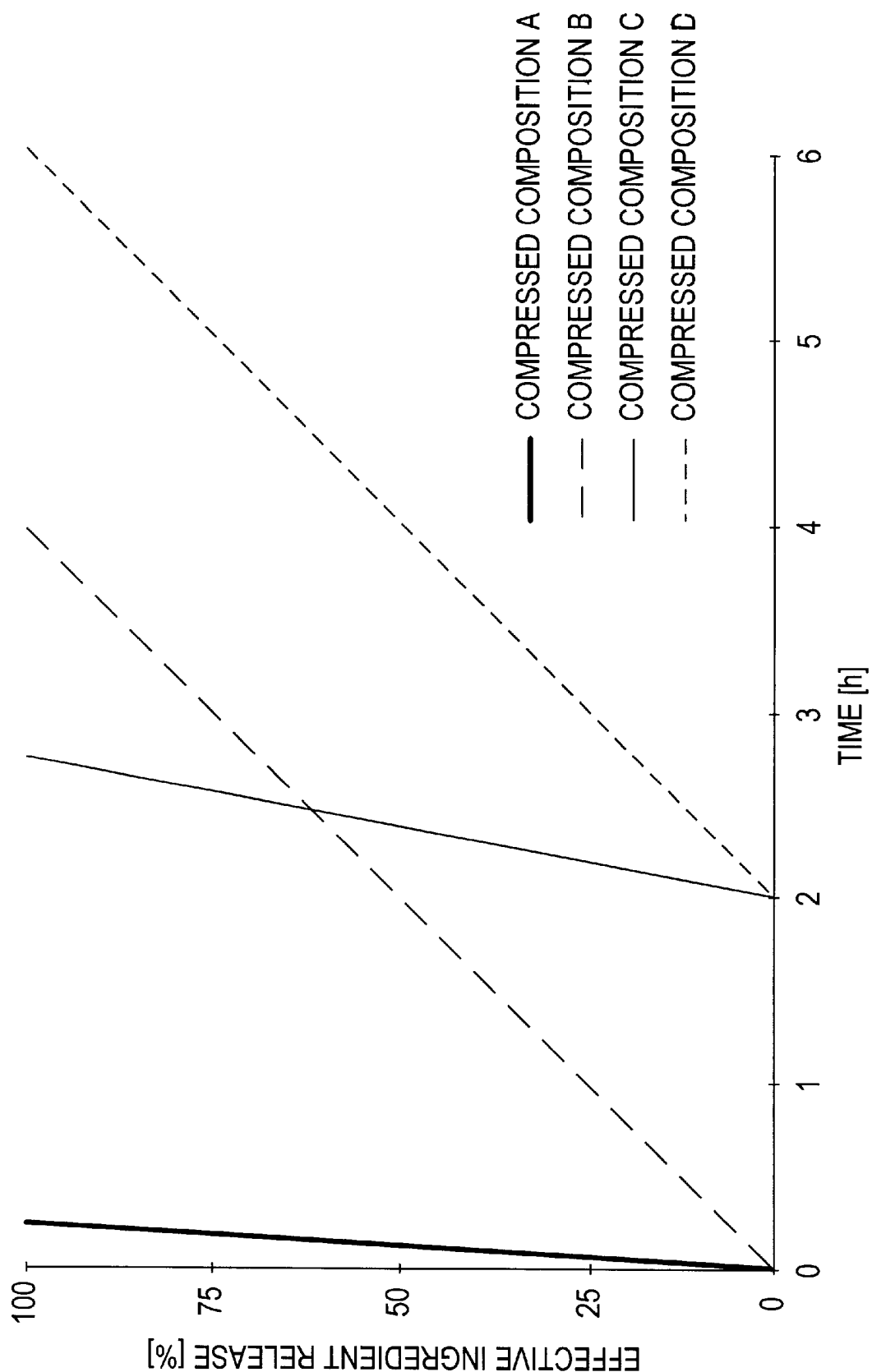
FIG. 1 is a graphical illustration of a release profile for effective ingredient release obtained with the aid of the compressed compositions A to D according to the invention.

Idealized model release profiles of the effective ingredients obtained with the respective compressed compositions A to D are shown in FIG. 1. The dependence of the percentage effective ingredient release on the time is shown in FIG. 1. Variation of the choice and number or amount of the compressed compositions obtains all the desired release profiles; twelve patterns are possible.

The administration of specific body hormones and substances related to them can be performed in an outstanding manner with the method according to the invention. A part of these specific body hormones are distinguished by a comparatively short dwell time in the body. These hormones include progesterone, testosterone, dehydro-epi-androsterone, estriol and estradiol. The level of other specific hormones follow an impressed circadian rhythm, i.e. their concentration in the blood varies over the course of 24 hours. For example, these hormones are: prednisone, prednisolone, dehydrocorticosterone, corticosterone, cortisol and aldosterone. Melatonin is, for example, predominantly secreted at night. Also the blood levels of analogs or inhibitory substances for these hormones can be subjected to a circadian rhythm. Examples of substance class are: antidiabetics, glucocorticoids, mineral corticoids and antihistamines.

To guarantee a constant level of effective ingredient for certain therapeutic goals, follow-up doses are frequently necessary in all cases.

Hormone effective ingredients can also be used in combinations. It can be required that each hormonal effective ingredient is either administered with a specific release profile or together in a joint release profile. For example these combinations of hormone effective ingredients can include progesterone/estradiol, testosterone/progesterone, progesterone/estriol, progesterone/estrone and cortisol/aldosterone.

The methods according to the invention make a perorally administered solid drug that provides all conceivable pharmaceutically required release profiles of effective ingredients or effective ingredient combinations. These methods allow a controllable manufacture. Reduced apparatus expenses and time-saving results from using the methods of the invention.

The invention will now be illustrated in more detailed with the following examples, which should not be considered as limiting the claims appended hereinbelow.

EXAMPLES

Effective Ingredient Release

The effective ingredient release and/or the release of the effective ingredient combination was measured in vitro in the following manner in the following examples according to the methods for testing cumulative release of effective ingredients described in U.S. Pat. No. 23 <724>.

| Apparatus: | according to DAB 96 V.5.4 (German version of U.S.P. 23 < 724 >) |
|---|---|
| Stirring speed: | 100 rpm ± 2 rpm |
| Temperature: | 37° C. ± 0.5 K |
| Medium volume: | 1000 ml |
| Medium: | 0.1 N HCl, 0.2 trisodium phosphate buffer, according to U.S.P. 23 < 724 >, Method A |

Example 1

Progesterone 50 mg, estradiol 1.6 mg
Goals of the Release Profile:

Pulsed release:

| Progesterone: | an initial rapid dose of 10 mg, After which uniformly delivered |
|---|---|
| Estradiol: | rapidly delivered |

| | Compressed Composition, mg | | |
|---|---|---|---|
| Formulation: | A | C | D |
| Progesterone | 10 | 10 | 30 |
| Estradiol | 1.6 | | |
| HPCM Type 2208‡* | | | 10 |
| Lactose | 20.9 | 22.5 | 9 |
| Corn starch | 12 | 12 | 5.5 |
| PVP K25‡ | 2 | 2 | 2 |
| Magnesium stearate | 0.5 | 0.5 | 0.5 |
| talcum | 1.5 | 1.5 | 1.5 |
| water (lost on drying) | 1.5 | 1.5 | 1.5 |
| Tablet | 50 mg φ 5 mm | 50 mg φ 5 mm | 60 mg φ 5 mm |

‡PVP K25 is polyvinyl propylene K-value = 25 (MW 27,000) according to "Coated Pharmaceutical Dosage Forms", K. H. Bauer, et al, CRC Press, Washington, D.C.; Scientific Publishers, Stuttgart, 1998, p. 230
‡*HPMC is hydroxypropyl methyl cellulose (a cellulose ether mixture) described in detail in "Coated Pharmaceutical Dosage Forms", K. H. Bauer, et al, CRC Press, Washington, D.C.; Scientific Publishers, Stuttgart, 1998, pp. 223 to 224.

| | Compressed Composition, mg | | |
|---|---|---|---|
| Coating: | A | C | D |
| Eudragit L30D† (total quantity of dry substance applied) | none | 7.5 | 7.5 |
| Talcum | | 1.75 | 1.75 |
| Triethyl citrate | | 0.75 | 0.75 |

†polymethacrylateacrylate

Preparation

Progesterone, estradiol, lactose, corn starch and hydroxypropylmethyl cellulose are mixed and granulated together with a solution of PVP in ethanol 96% granulated. The granulate is dried, mixed with talcum and magnesium stearate and pressed into a tablet of predetermined diameter and mass. The coating is applied to the tablet in a suitable apparatus by means of a dispersion of Eudragit, talcum and triethyl citrate and dried.

The compressed composition so made is packaged in a capsule.

TABLE 1

In vitro Release of Effective Ingredient (accumulate)

| | Compressed Compositions, mg | | | | Entire Drug, mg | |
|---|---|---|---|---|---|---|
| | A | | C | D | | |
| Time, h | Prg* | est* | prg | prg | prg | est |
| 0.25 | 10 | 1.6 | 0 | 0 | 10 | 1.6 |
| 1. | 10 | 1.6 | 0 | 0 | 10.0 | 1.6 |
| 2. | 10 | 1.6 | 0 | 0 | 10.0 | 1.6 |
| 2.5 | 10 | 1.6 | 10 | 3.2 | 23.2 | 1.6 |
| 3 | 10 | 1.6 | 10 | 7.0 | 27.0 | 1.6 |
| 4 | 10 | 1.6 | 10 | 15.2 | 35.2 | 1.6 |
| 5 | 10 | 1.6 | 10 | 23.8 | 43.8 | 1.6 |
| 6 | 10 | 1.6 | 10 | 30 | 50 | 1.6 |

*prg = progesterone and est = estradiol

Figure 2:
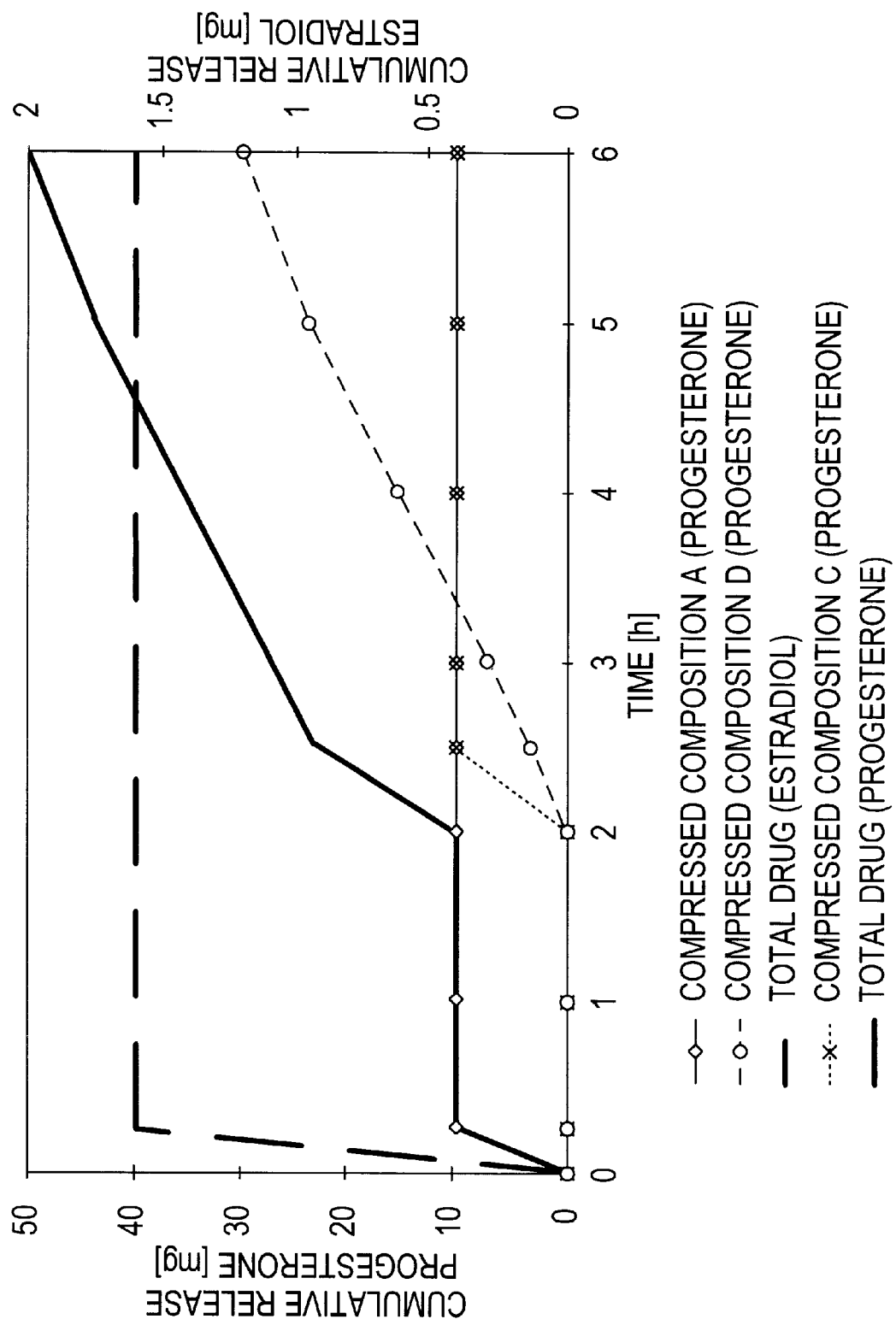
FIG. 2 is a graphical illustration of the release profile of the effective ingredients, progesterone and estradiol, i.e. the dependence of their release rates on the time.

FIG. 2 shows the release profile for the effective ingredients progesterone and estradiol which is tabulated in Table 1. The dependence of the amount released on time is shown for the individual compressed compositions and the entire drug.

Three compressed compositions were used as follows:

Compressed composition A, 10 mg progesterone, 1.6 mg estradiol;
Compressed composition C, 10 mg progesterone; and
Compressed composition D, 30 mg progesterone.

Each effective ingredient component is administered with its own release profile.

A rapid effective ingredient delivery of 10 mg progesterone and 1.6 mg estradiol occurs by means of the compressed composition A after 0.25 h, a delayed release of 10 mg progesterone after 2.5 h occurs by means of the compressed composition C and a delivery of effective ingredient which combines a delayed release with a uniformly maintained release of 30 mg progesterone occurs by means of the compressed composition D after 6 h.

Example 2

Melatonin 10 mg
Goal of the Release Profile:
Pulsatile Release of Melatonin

| | Compressed Composition, mg | | |
|---|---|---|---|
| Formulation: | A | B | D |
| Melatonin | 2.5 | 2.5 | 2.5 |
| HPMC Type 2208‡* | | 5 | 5 |
| Lactose | 26.5 | 22.5 | 20 |
| Corn starch | 15 | 15 | 15 |
| PVP K25‡ | 1.5 | 1.5 | 1.5 |
| Magnesium stearate | 0.5 | 0.5 | 0.5 |

-continued

| | Compressed Composition, mg | | |
|---|---|---|---|
| Formulation: | A | B | D |
| talcum | 1.5 | 1.5 | 1.5 |
| carboxymethyl-cellulose sodium | 1 | | |
| water (lost on drying) | 1.5 | 1.5 | 1.5 |
| Tablet | 50 mg φ 5 mm | 50 mg φ 5 mm | 50 mg φ 5 mm |

‡PVP K25 is polyvinyl propylene K-value = 25 (MW 27,000) according to "Coated Pharmaceutical Dosage Forms", K. H. Bauer, et al, CRC Press, Washington, D.C.; Scientific Publishers, Stuttgart, 1998, p. 230
‡*HPMC is hydroxypropyl methyl cellulose (a cellulose ether mixture) described in detail in "Coated Pharmaceutical Dosage Forms", K. H. Bauer, et al, CRC Press, Washington, D.C.; Scientific Publishers, Stuttgart, 1998, pp. 223 to 224.

| | Compressed Composition, mg | | |
|---|---|---|---|
| Coating: | A | B | D |
| Eudragit L30D† (total quantity of dry substance applied) | none | none | 3.76 |
| Talcum | | | 0.81 |
| Glycerol triacetate | | | 0.38 |
| Anti-foaming emulsion | | | 0.05 |

†polymethacrylateacrylate

Preparation

Melatonin, lactose, corn starch and hydroxypropylmethyl cellulose are mixed and granulated together with a solution of PVP in ethanol 96% granulated. The granulate is dried, mixed with talcum and magnesium stearate and pressed into a tablet of predetermined diameter and mass. The coating is applied to the tablet in a suitable apparatus by means of a dispersion of Eudragit, talcum and triethyl citrate and dried.

The compressed composition so made is packaged in a capsule.

TABLE 2

In vitro Release of Melatonin Ingredient (accumulate)

| | Compressed Compositions, mg | | | |
|---|---|---|---|---|
| Time, h | A Melatonin | B Melatonin | D Melatonin | Entire Drug, mg |
| 0.17 | 2.5 | 0 | 0 | 2.48 |
| 1. | 2.5 | 1.03 | 0 | 3.51 |
| 2. | 2.5 | 1.65 | 0.14 | 4.26 |
| 3 | 2.5 | 2.13 | 2.14 | 6.75 |
| 4 | 2.5 | 2.5 | 4.65 | 9.51 |
| 5 | 2.5 | 2.5 | 4.89 | 9.75 |
| 6 | 2.5 | 2.5 | 5 | 10 |

Figure 3:
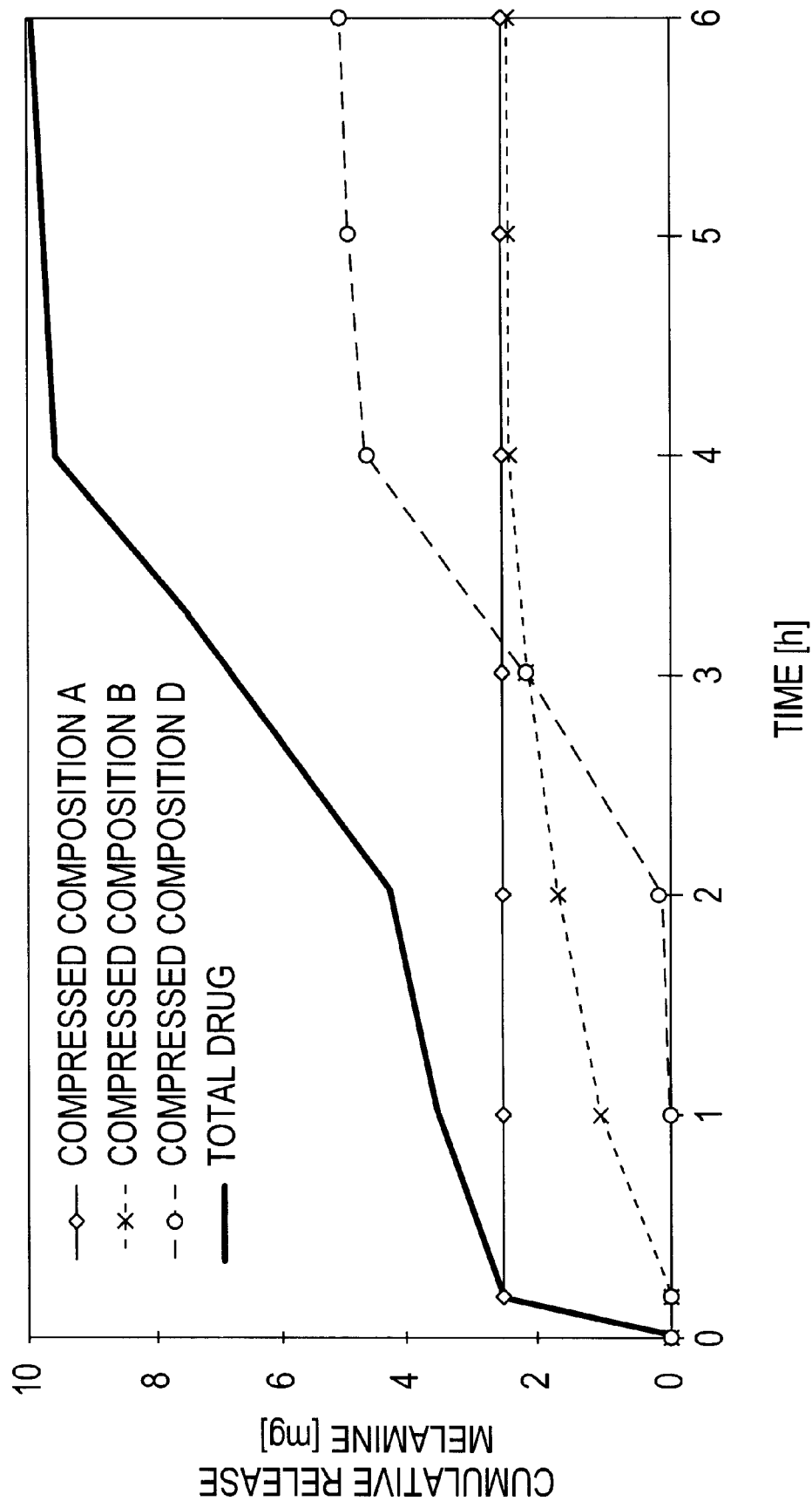
FIG. 3 is a graphical illustration of the release profile of the effective ingredient, melatonin, i.e. the dependence of its release rate on the time.

FIG. 3 shows the release profile for the effective ingredient, melatonin, which is tabulated in Table 2. The dependence of the amount released on time is shown for the individual compressed compositions and the entire drug.

Three compressed compositions were used as follows:
Compressed composition A, 2.5 mg melatonin;
Compressed composition B, 2.5 mg melatonin; and
Compressed composition D, 5 mg melatonin.

A rapid effective ingredient delivery of 2.5 mg melatonin occurs by means of the compressed composition A after 0.17 h, a uniformly maintained delivery, i.e. delivery at a constant rate, of 2.5 mg melatonin after 4 h occurs by means of the compressed composition B and a delivery of 5 mg melatonin which combines a delayed release with a uniformly maintained release occurs by means of the compressed composition D after 6 h.

Example 3

Hydrocortisone 10 mg
Goal of the Release Profile:
Uniformly maintained Release of Hydrocortisone

| Formulation: | Compressed Composition, mg | | |
|---|---|---|---|
| | A | B | D |
| Hydrocortisone | 1 | 3 | 6 |
| HPMC Type 2208‡* | | 5 | 5 |
| Lactose | 27 | 22 | 19 |
| Corn starch | 16 | 15 | 15 |
| PVP K25‡ | 1.5 | 1.5 | 1.5 |
| Magnesium stearate | 0.5 | 0.5 | 0.5 |
| talcum | 1.5 | 1.5 | 1.5 |
| carboxymethyl cellulose sodium | 1 | | |
| water (lost on drying) | 1.5 | 1.5 | 1.5 |
| Tablet | 50 mg ϕ 5 mm | 50 mg ϕ 5 mm | 50 mg ϕ 5 mm |

‡PVP K25 is polyvinyl propylene K-value = 25 (MW 27,000) according to "Coated Pharmaceutical Dosage Forms", K. H. Bauer, et al, CRC Press, Washington, D.C.; Scientific Publishers, Stuttgart, 1998, p. 230
‡*HPMC is hydroxypropyl methyl cellulose (a cellulose ether mixture) described in detail in "Coated Pharmaceutical Dosage Forms", K. H. Bauer, et al, CRC Press, Washington, D.C.; Scientific Publishers, Stuttgart, 1998, pp. 223 to 224.

| Coating: | Compressed Composition, mg | | |
|---|---|---|---|
| | A | B | D |
| Eudragit L30D† (total quantity of dry substance applied) | none | none | 3.76 |
| Talcum | | | 0.81 |
| Glycerol triacetate | | | 0.38 |
| Anti-foaming emulsion | | | 0.05 |

†polymethacrylateacrylate

Preparation

Hydrocortisone, lactose, corn starch and hydroxypropylmethyl cellulose are mixed and granulated together with a solution of PVP in ethanol 96% granulated. The granulate is dried, mixed with talcum and magnesium stearate and pressed into a tablet of predetermined diameter and mass. The coating is applied to the tablet in a suitable apparatus by means of a dispersion of Eudragit, talcum and triethyl citrate and dried.

The compressed composition so made is packaged in a capsule.

TABLE 3

In vitro Release of Hydrocortisone (accumulate)

| | Compressed Compositions, mg | | | |
|---|---|---|---|---|
| Time, h | A Hydrocortisone | B Hydrocortisone | D Hydrocortisone | Entire Drug, mg |
| 0.25 | 1 | 0 | 0 | 1.06 |
| 1. | 1 | 0.9 | 0 | 1.86 |
| 2. | 1 | 2.1 | 0 | 3.06 |
| 2.47 | 1 | 2.3 | 0.8 | 4.13 |
| 3 | 1 | 2.6 | 1.7 | 5.32 |
| 4 | 1 | 3 | 3.1 | 7.07 |
| 5 | 1 | 3 | 4.4 | 8.38 |
| 6 | 1 | 3 | 6 | 10 |

Figure 4:
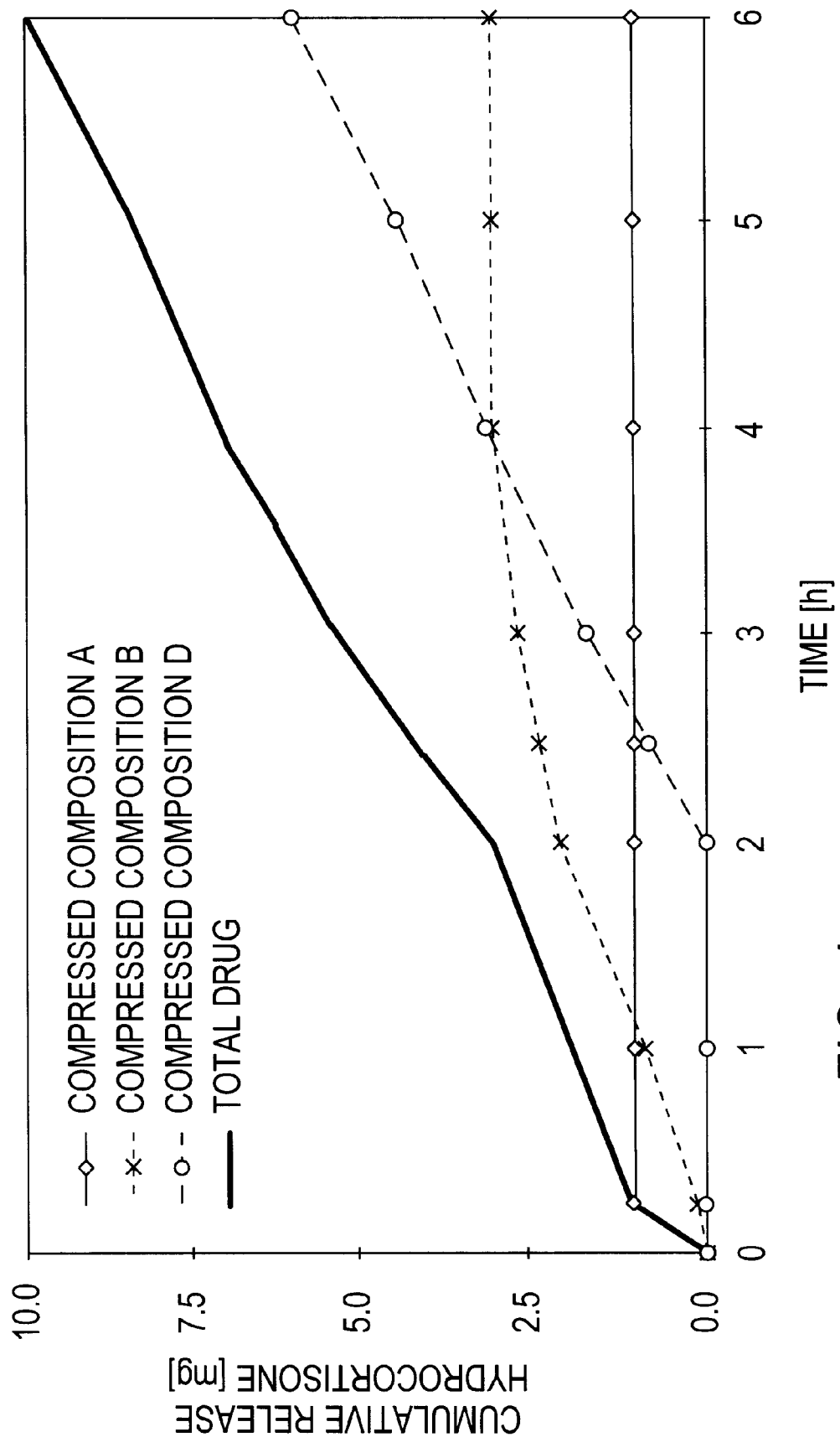
FIG. 4 is a graphical illustration of the release profile of the effective ingredient, hydrocortisone, i.e. the dependence of their release rates on the time.

FIG. 4 shows the release profile for the effective ingredient, hydrocortisone, which is tabulated in Table 3. The dependence of the amount released on time is shown for the individual compressed compositions and the entire drug.

Three compressed compositions were used as follows:
Compressed composition A, 1 mg hydrocortisone;
Compressed composition B, 3 mg hydrocortisone; and
Compressed composition D, 6 mg hydrocortisone.

A rapid effective ingredient delivery of 1 mg hydrocortisone occurs by means of the compressed composition A after 0.25 h, a uniformly maintained delivery, i.e. delivery at a constant rate, of 3 mg hydrocortisone after 4 h occurs by means of the compressed composition B and a delivery of 6 mg hydrocortisone which combines a delayed delivery with a uniformly maintained delivery occurs by means of the compressed composition D after 6 h.

The disclosure of German Patent Application 197 18 012.4 of Apr. 29, 1997 is hereby explicitly incorporated by reference. This German Patent Application discloses the same invention as described herein and claimed in the claims appended hereinbelow and is the basis for a claim of priority for the instant invention under 35 U.S.C. 119. While the invention has been illustrated and described as embodied in a method of making a solid drug with controlled effective ingredient delivery for oral administration, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A method of making a solid drug with controlled effective ingredient delivery for oral administration, said method comprising the steps of:
   a) providing respective pluralities of compressed compositions of four different types having respective different amounts and/or types of effective ingredients and/or effective ingredient combinations therein;
   b) selecting a predetermined number of the compressed compositions from at least three different ones of the four different types;

c) mixing the compressed compositions selected in step b) with a pharmaceutically compatible auxiliary substance and/or carrier substance to form a mixture;

d) granulating the mixture to form a granulate and forming tablets from the granulate; and e) coating the tablets formed from the granulate;

so that a predetermined pharmaceutically-required release profile for the effective ingredient and/or the effective ingredient combination results when the solid drug is administered orally;

wherein a first (A) of the compressed compositions is formed to deliver at least 75% of the effective ingredient and/or the effective ingredient combination contained therein within 45 minutes;

wherein a second (B) of the compressed compositions is formed to deliver 100% of the effective ingredient and/or effective ingredient combination contained therein at the earliest within 3 hours according to an approximately zero-order release profile by means of hydrophilic matrix tablets with diffusion controlling lacquer coatings or lipophilic matrix tablets;

wherein a third (C) of the compressed compositions is formed to deliver at least 75% of the effective ingredient and/or the effective ingredient combination contained therein in the duodenum and intestine within 45 minutes after a pH change from 6 to 7.5 by means of a gastric-juice-resistant coating; and wherein a fourth (D) of the compressed compositions is formed to deliver 100% of the effective ingredient and/or effective ingredient combination contained therein in the duodenum and intestine at the earliest three hours after a pH change from 6 to 7.5 according to a zero-order release profile by means of gastric-juice resistant matrix tablets or combinations of gastric-juice resistance with diffusion-controlled lacquer coatings.

2. The method as defined in claim 1, wherein the solid drug is administered in a capsule.

3. The method as defined in claim 1, wherein said compressed compositions each have a weight of from 30 to 600 mg.

4. The method as defined in claim 1, wherein said compressed compositions each have a weight of from 40 to 100 mg.

5. The method as defined in claim 1, wherein said predetermined number is a positive integer up to 30.

6. The method as defined in claim 5, wherein said compressed compositions each have a weight of from 40 to 100 mg.

7. The method as defined in claim 1, whereby the solid drug has a total weight of up to 1 gram and said predetermined number is up to 30.

8. A solid drug made by the method of claim 1.

* * * * *